(12) United States Patent
Cassaday

(10) Patent No.: US 7,378,978 B2
(45) Date of Patent: May 27, 2008

(54) CHAIR OR BED MEMBER HAVING DATA STORAGE

(76) Inventor: Terry Cassaday, 5616 McAdam Rd., Mississauga, Ontario (CA) L4Z 1P2

( * ) Notice: Subject to any disclaimer, the term of this patent is extended or adjusted under 35 U.S.C. 154(b) by 984 days.

(21) Appl. No.: 10/374,429

(22) Filed: Feb. 27, 2003

(65) Prior Publication Data

US 2003/0130582 A1 Jul. 10, 2003

(51) Int. Cl.
*G08B 21/00* (2006.01)
(52) U.S. Cl. .............. 340/667; 340/539.12; 297/217.2; 297/217.4
(58) Field of Classification Search ................. 340/667
See application file for complete search history.

(56) References Cited

U.S. PATENT DOCUMENTS

| 4,698,571 | A | * | 10/1987 | Mizuta et al. | ........... 318/568.1 |
| 5,683,137 | A | * | 11/1997 | McDonald et al. | ...... 297/217.3 |
| 5,724,990 | A | * | 3/1998 | Ogino | ........................ 600/587 |
| 5,978,976 | A | * | 11/1999 | Chai | ............................. 4/483 |
| 6,239,706 | B1 | * | 5/2001 | Yoshiike et al. | .......... 340/573.4 |
| 6,560,803 | B2 | * | 5/2003 | Zur | ............................... 5/654 |
| 2004/0129478 | A1 | * | 7/2004 | Breed et al. | ................ 180/273 |

* cited by examiner

Primary Examiner—George Bugg

(57) ABSTRACT

A chair or bed member has data storage of information regarding the chair or bed member. The chair or bed member further has a sensor which senses physical movement by a person using the chair or bed member to produce an output of the information from the data storage.

36 Claims, 5 Drawing Sheets

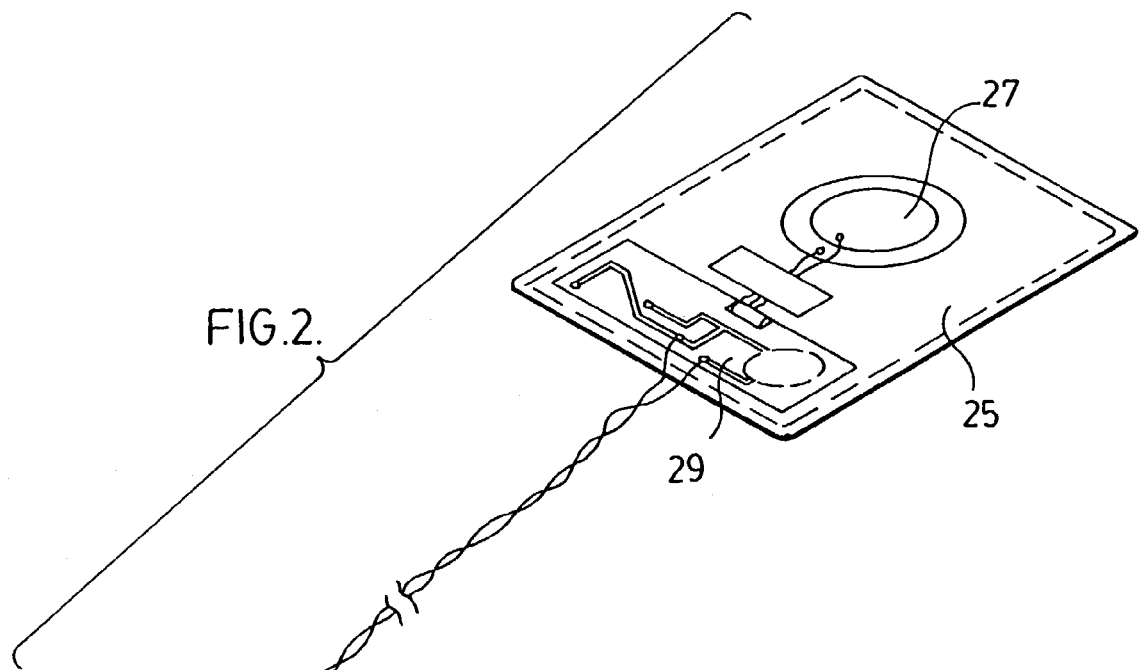
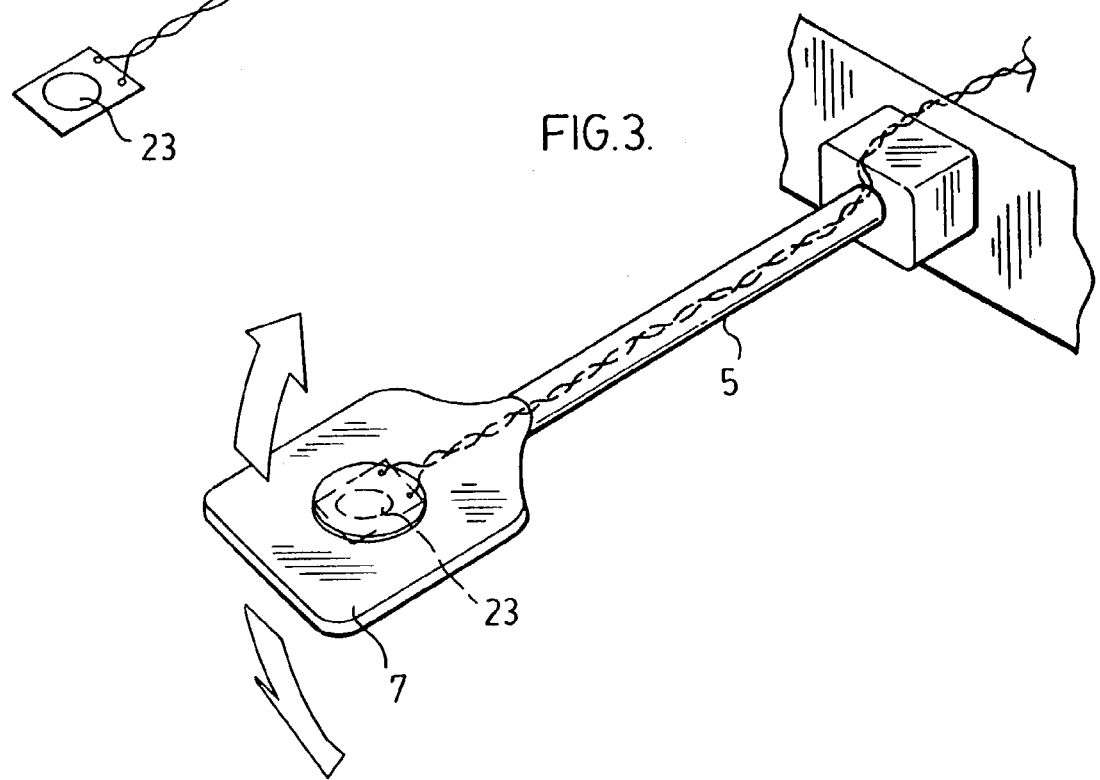

CHAIR OR BED MEMBER HAVING DATA STORAGE

FIELD OF THE INVENTION

The present invention relates to a chair or bed member having moving parts and controls for those moving parts.

BACKGROUND OF THE INVENTION

A comfortable sitting or lying position for one person may not be comfortable for another person. Furthermore, people come in all different shapes and sizes. Accordingly, essentially all up to date office chairs have numerous different moveable parts to accommodate for different people. Each of these parts typically has its own control.

The same is true of adjustable lounge chairs and even for some of the newly designed adjustable beds.

When a person purchases anyone of the above items, the item will come with some type of manual describing proper use of the item. At this point, there is generally no concern that the person using the chair or bed member will not know how to set the proper positions for the different moveable parts.

There are however times when set up operation is not as apparent. For example, when a second person wishes to use the chair or bed or even when the person who set it up has not used the chair or bed for an extended period of time the operation of the controls can become confusing.

There are also times where one wishes to re-order a product such as for example, an office chair or the like without being able to immediately lay his/her hands on the required information for re-ordering purposes.

SUMMARY OF THE PRESENT INVENTION

The present invention relates to a chair or bed member which overcomes the drawbacks noted above. More particularly, the chair or bed member of the present invention is one which has data storage means containing information regarding the chair or bed member and further has a physical movement sensing means which produces an output of the information from the data storage means.

According to an aspect of the invention the data storage means comprises a computer chip and the physical movement sensing means comprises a pressure sensor to produce the output from the computer chip. This output can be either audible or visual.

According to another aspect of the invention the chair or bed member has different moveable parts with controls for those parts. The data storage means contains information as to how to use the controls.

According to another aspect of the invention the data storage means contains information as to the history of the chair or bed member which can be used for example, for re-ordering purposes.

BRIEF DESCRIPTION OF THE DRAWINGS

The above as well as other advantages and features of the present invention will be described in greater detail according to the preferred embodiments of the present invention in which;

FIG. 2 is perspective view looking down on a sensor and information containing system from the chair of FIG. 1.

FIG. 3 is a perspective view showing the mounting of the sensor in the chair of FIG. 1.

DETAILED DESCRIPTION ACCORDING TO THE PREFERRED

Figure 1:
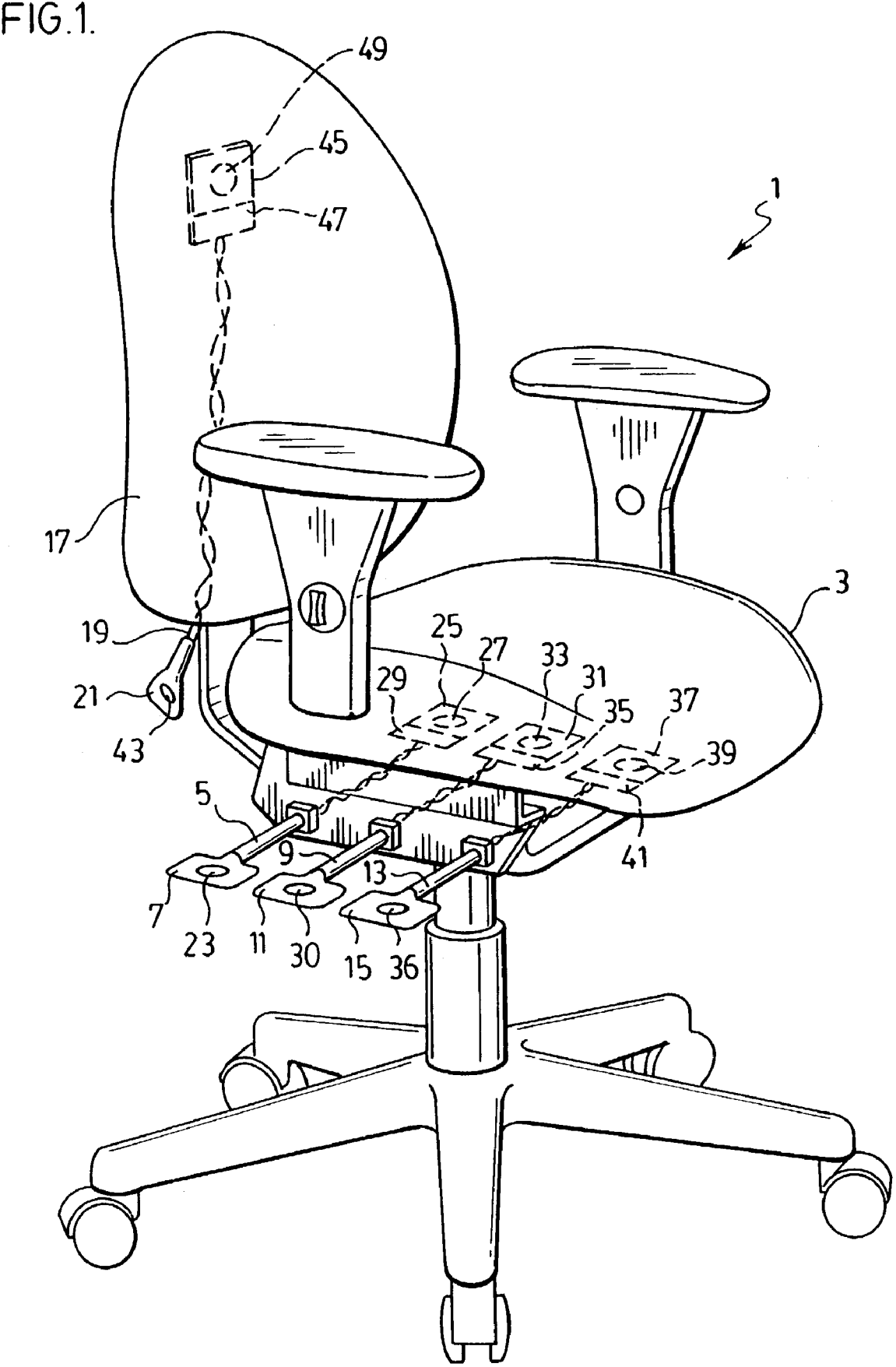
FIG. 1 is a perspective view of an office chair made in accordance with a preferred embodiment of the present invention.

Embodiments of the present invention in which:

FIG. 1 shows an office type chair generally indicated at 1. This chair has a chair seat 3 and a chair back 17. Both the seat and the back of the chair are moveable to different positions of use of the chair. These different portions allow the person using the chair to assume different ergonomically desirable body positions when seated in the chair.

More particularly, seat 3 is adjusted by means of lever controls 5, 9 and 13. Each of these lever controls includes a control paddle 7, 11 and 15 respectively.

The chair back is adjustable by means of a lever 19 having a control paddle 21.

Each of the above lever controls, with associated paddle, controls a different adjustment such as for example, height or angle adjustment for the chair seat and angle adjustment for the chair back. The actual manner of making the adjustment through the appropriate control is typically something that is learned by the initial user of the chair during set-up but not necessarily known to a second user of the chair or possibly forgotten over time by the initial user of the chair.

In accordance with the present invention the chair itself includes operating instructions for the control.

More particularly, the chair includes its own data storage means and a physical movement sensor to produce an output from the data storage means. In the preferred embodiment shown the data storage means comprises preprogrammed computer chips with pressure sensors for producing an output from the computer chips.

In chair 1 a plurality of chip boards 25, 31 and 37 are mounted to the underside of the chair seat. Pressure sensors 23, 30 and 36 wired to the respective chip boards are located within the paddles 7, 11 and 15 as shown in FIG. 1.

The chip boards 25, 31 and 37 further include small speakers 27, 33 and 39.

A further chip board 45 carrying a pre-programmed computer chip 47 and a speaker 49 is mounted to the rear of the chair back. A pressure sensor 43 located in paddle 21 is wired to chip board 45.

With the user sitting in the chair he or she can press on any one of the pressure sensors and the associated computer chip will then provide an audible output as to operation of the lever in which the pressure sensor is mounted. This eliminates any guess work in how to set the chair up properly.

It is to be understood that if the chair user does not need directions the controls can be manipulated without having to push on any of the pressure sensors.

It is also to be appreciated that other types of physical movements sensors such as heat or light sensors could be used in the controls. When the person moves his or her hands close to or over these types of sensors they will also produce an output from the programmed chips.

FIG. 2 shows in more detail pressure sensor 23 wired to chip board 25 carrying programmed chip 29 and speaker 27.

FIG. 3 shows how the wiring between the pressure sensor and the chip board fits through the hollow interior of the lever 5 from the lever paddle 7 to the chair base. Accordingly, the levers provide a protective covering for what would otherwise be open, unsightly wiring on the chair.

Figure 4:
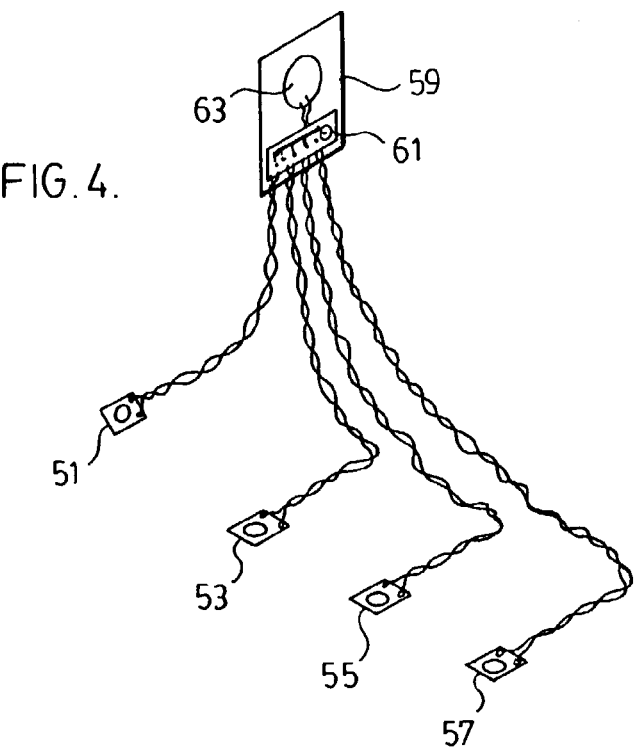
FIGS. 4 through 6 show a different sensing and data storage set-ups according to different preferred embodiments of the present invention.

In lieu of using a plurality of separate chips and chip boards, FIG. 4 demonstrates that a plurality of sensors 51, 53, 55 and 57 can all be hooked into one board 59 containing a single chip 61 programmed with information regarding all of the controls. The pressure sensors themselves would once again be located at the individual control paddles. A single speaker 63 would provide the audible output of the chair operation information.

Figure 5:
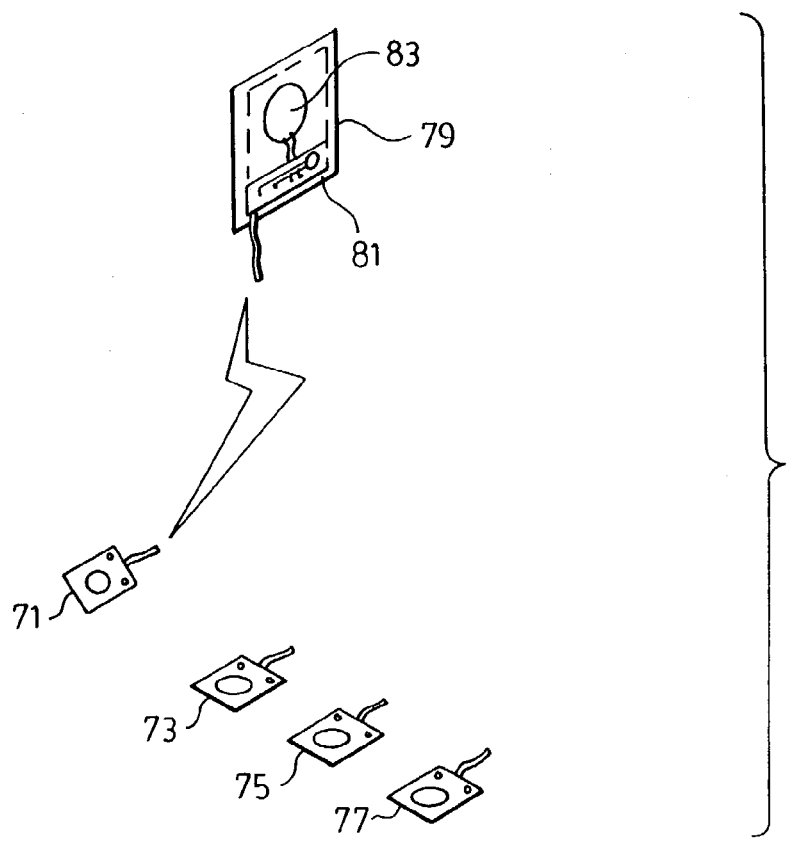

FIG. 5 demonstrates a principal similar to FIG. 4 with the exception that a plurality of sensors generate airborne rather than hard wire signals to a chip board 79 carrying a computer chip 81 and a speaker 83 for outputting from chip 81.

All of the description above relates to an audible output from the computer chip data storage in the chair. However, it is to be easily understood from FIG. 5 that anyone of the sensors 71 through 77 could generate signals for a video output by means of a display screen which could be either on board or remote of the chair. A particularly good system is one in which the output is visually displayed on a computer monitor which is operated from the chair.

Figure 6:
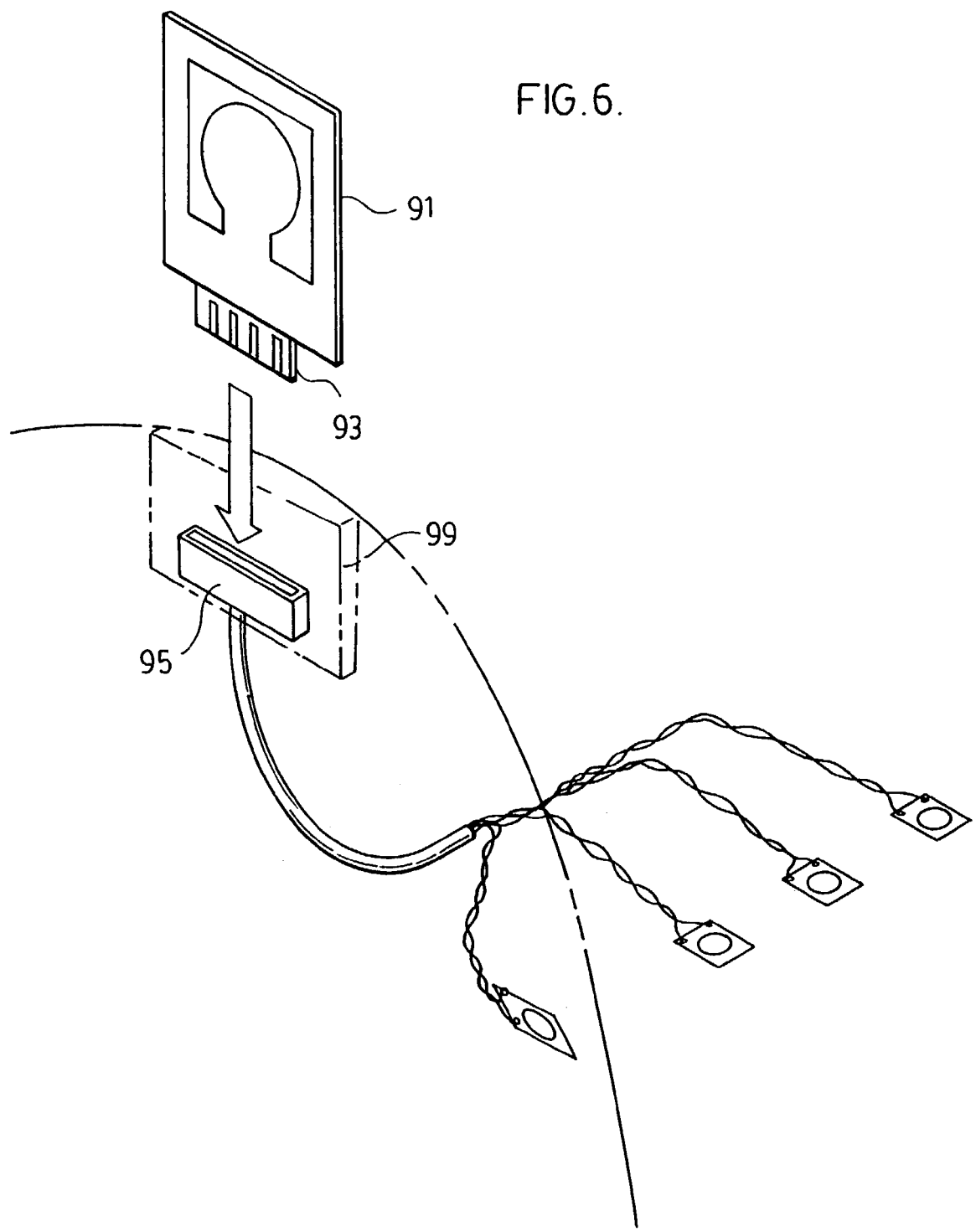

Over time the small battery carried by the chip board for its operation will eventually fail. FIG. 6 of the drawings shows a replaceable chip board 91 having a male contact end 93 which plugs into a socket 95 wired back to a plurality of sensors shown in FIG. 6. This chip board, once its life has expired, can easily be replaced by a new chip board.

Note that in FIG. 6, chip board 91 seats within a pocket 99 located high on the back of the chair. Pocket 99 acts to effectively hide the chip board, is in a location almost level with the head of the chair user so that the user can easily hear the instructions from the small speaker on the chip board.

In the description above, reference is made to each of the controls including directions as to how to use the controls. According to a further aspect of the invention the information carried in any one or all of the chips can be history information regarding the chair. For example, any one of the chips can identify serial number, the manufacturer or even the construction of the chair. This allows for easy re-ordering of the chair.

Figure 7:
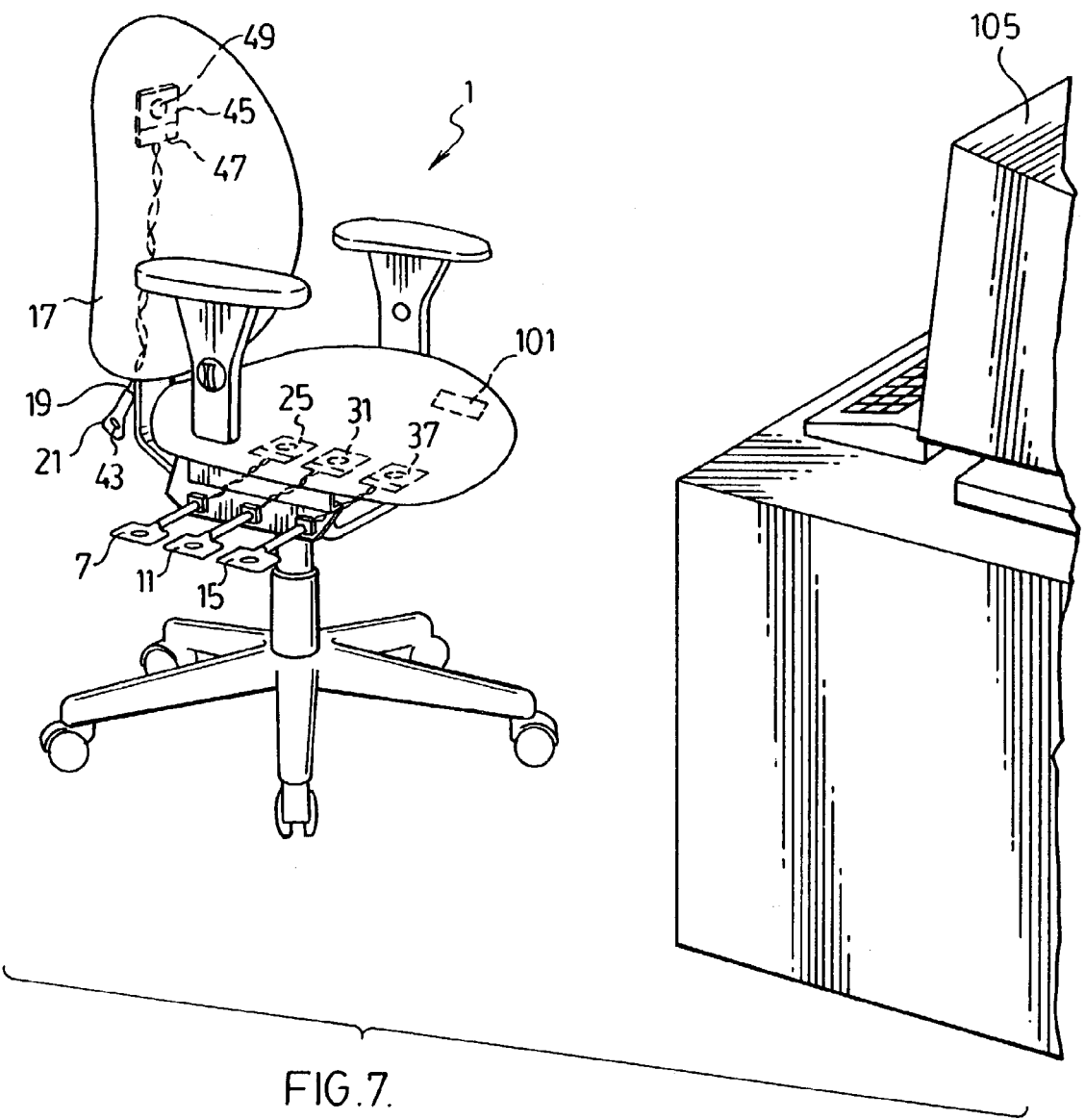
FIG. 7 shows an office chair incorporating further features according to still another embodiment of the invention.

FIG. 7 shows another embodiment of the invention in which the chair includes an additional sensor 101. This sensor is buried slightly below the surface of the seat of the chair, it is located in the area such that it would be directly below the back of the thigh of a person sitting in the chair. It can equally as well be buried in the armrest of the chair where a person would place his or her forearm. These are two areas of the body from which a person's biorhythms indicating things such as heart rate, blood pressure, etc. can be felt. The sensor picks up these biorhythms and they are then output from the sensor.

In the set shown in FIG. 7, the chair is used to seat a person to use of computer 105. This computer is programmed to accept and display the output from sensor 101. In this way the person using the chair can easily obtain a medical check-up by simply sitting in the chair.

If the person does not want such information every time he or she sits in the chair the bio feedback system can simply be turned off at the computer.

It is to be further understood that although the description is specific to an office chair the concept of the invention equally applies to any type of a chair, lounge or bed having moving parts. Accordingly, although various preferred embodiments of the present invention have been described, it is to be appreciated that variations may be made without departing from the spirit of the invention or the scope of the appended claims.

The embodiments of the invention in which an exclusive property or privilege is claimed are defined as follows:

1. A chair or bed member having a) moving parts; b) controls for said moving parts; and c) data storage means containing information regarding the member and information regarding operation of said controls further; d) said member further having physical movement sensing means which produces an output of the information regarding the member and operation of said controls from the data storage means.

2. A chair or bed member as claimed in claim 1 wherein said data storage means comprises a plurality of programmed computer chips, one for each control.

3. A chair or bed member as claimed in claim 2 wherein said physical movement sensing means comprises a plurality of pressure sensors, said pressure sensors being located at said controls.

4. A chair or bed member having data storage means containing information regarding the member and further having physical movement sensing means which produces an output of the information from the data storage means wherein said member has moving parts and controls for said moving parts, said data storage means containing information regarding operation of said controls wherein said controls comprise levers with paddles on said levers said pressure sensors being provided within said paddles.

5. A chair or bed member as claimed in claim 1 further including speakers for audibly providing the output of the information from the data storage means.

6. A chair or bed member as claimed in claim 1 wherein said data storage means outputs to a visual display.

7. A chair or bed member as claimed in claim 6 wherein said visual display is remote from said member.

8. A chair or bed member as claimed in claim 6 wherein said visual display is on board the member.

9. A chair or bed member having data storage means containing information regarding the member and further having physical movement sensing means which produces an output of the information from the data storage means wherein said member has moving parts and controls for said moving parts, said data storage means containing information regarding operation of said controls wherein the data storage means contains information regarding origin of the member.

10. A chair or bed member having data storage means containing information regarding the member and further having physical movement sensing means which produces an output of the information from the data storage means wherein said member has moving parts and controls for said moving parts, said data storage means containing information regarding operation of said controls wherein the data storage means contains information regarding construction of the member.

11. A chair or bed member as claimed in claim 1 wherein said data storage means comprises a computer chip and wherein said physical movement sensing means comprises a plurality of pressure sensors, one for each of said controls, the output produced by said computer chip being dependent upon selection of one of said pressure sensors.

12. A chair or bed member as claimed in claim 11 wherein said member includes a speaker to audibly produce the output from said computer chip, the speaker being mounted on a board with said computer chip, the board being replaceably secured in a hidden location on said member.

13. A chair or bed member as claimed in claim 12 wherein said member has a seat part and a back part, said board being hidden within a pocket high on said back part of said member.

14. A chair or bed member as claimed in claim 1 wherein said data storage means comprises a programmed computer chip and said physical movement sensing means comprises a pressure sensor located remotely of and transmitting an air borne signal to said computer chip for producing the Output of the information from the computer chip.

15. A chair or bed member including moveable parts and controls which are mounted on said member and which provide movement of said moveable parts, said member further including data storage means containing instructional information regarding operating functions of said controls and physical movement sensing switch means which, when activated, produces an output of the instructional information without producing operation of said controls for said moveable parts of said member.

16. A chair or bed member as claimed in claim 15 wherein said physical movement switch means comprises a plurality of switches, each of said controls being provided with one of said switches, the switches being located directly at the controls.

17. A chair or bed member as claimed in claim 16 wherein said controls comprise levers with paddles on the levers, the switches comprising pressure sensors provided on the paddles of the controls.

18. A chair or bed member as claimed in claim 15 wherein the output of the information comprises a visual output viewable at a visual display.

19. A chair or bed member as claimed in claim 18 wherein said visual display is provided on said member.

20. A chair or bed member as claimed in claim 18 wherein said visual display is located remotely of said member.

21. A chair or bed member as claimed in claim 20 wherein said member has a wireless feed to said visual display.

22. A chair or bed member as claimed in claim 15 wherein the output of the information comprises an audio output.

23. A chair or bed member as claimed in claim 22 wherein said physical movement switch means comprises a switch at each of said controls, said audio output being provided through a plurality of speakers provided on said member, each speaker being electronically linked with an individual one of said controls.

24. A chair or bed member as claimed in claim 22 wherein said audio output is provided through a single speaker.

25. A chair or bed member as claimed in claim 24 wherein said speaker is mounted on board of said member.

26. A chair or bed member as claimed in claim 24 wherein said speaker is located remotely of said member.

27. A chair or bed member as claimed in claim 26 wherein said member has a wireless feed of said audio output from said member to said speaker.

28. A chair or bed member including data storage means for storing both instructional and operational information regarding the member and sensing means, which when activated outputs the instructional information regarding the member.

29. A chair or bed member as claimed in claim 28 wherein said sensing means comprise physical movement sensing means.

30. A chair or bed member as claimed in claim 29 wherein said output comprises an audio output through a speaker mounted on a board of said member.

31. A chair or bed member as claimed in claim 30 wherein said data storage means has a wireless feed to said speaker.

32. A chair or bed member as claimed in claim 28 wherein said output comprises a visual output through a visual display.

33. A chair or bed member as claimed in claim 32 wherein said visual display is located remotely of said member.

34. A chair or bed member as claimed in claim 32 wherein said visual display is provided on board of said member.

35. A chair or bed member as claimed in claim 33 wherein said data storage means has a wireless feed to said visual display.

36. A chair or bed member having:
  a) moveable parts;
  b) controls for said moving parts;
  c) data storage means containing:
    i) operational information regarding the member, and
    ii) instructional information regarding the controls for said moving parts; and
  d) sensing means which when activated outputs instructional information regarding the controls, wherein said member has moving parts and controls for said moving parts, said data storage means containing information regarding operation of said controls.

* * * * *